US007459599B2

(12) United States Patent
Tamura et al.

(10) Patent No.: US 7,459,599 B2
(45) Date of Patent: Dec. 2, 2008

(54) METHODS FOR PRODUCING PROTEINS USING SILKWORM MIDDLE SILK GLAND-SPECIFIC GENE EXPRESSION SYSTEM

(75) Inventors: Toshiki Tamura, Tsukuba (JP); Hideki Sezutsu, Tsukuba (JP); Isao Kobayashi, Tsukuba (JP); Katsura Kojima, Tsukuba (JP); Toshio Kanda, Tsukuba (JP); Keiro Uchino, Tsukuba (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 0 days.

(21) Appl. No.: 11/085,838

(22) Filed: Mar. 21, 2005

(65) Prior Publication Data

US 2006/0070132 A1    Mar. 30, 2006

(30) Foreign Application Priority Data

Sep. 27, 2004   (JP)   ............................. 2004-279527
Mar. 15, 2005   (JP)   ............................. 2005-072401

(51) Int. Cl.
*C12P 2/00*    (2006.01)
*C12N 15/00*   (2006.01)
*A01K 67/00*   (2006.01)

(52) U.S. Cl. .................................. 800/4; 800/22; 800/8
(58) Field of Classification Search ..................... 800/4, 800/22, 8
See application file for complete search history.

(56) References Cited

OTHER PUBLICATIONS

Pdersen et al. Computers and Chemistry, 23:191-207; 1999.*
Tomita et al. (Nature Biotech. 21: 52-56; 2003.*
Matsuno et al. J. Biol. Chem. 264:18707-18713; 1989.*
Imamura et al. (Genetics 165:1329-1340; 2003.*
Kunze et al. (Biochim. Biophys. Acta 1410:287-298; 1999.*
Horn et al., "Highly Sensitive, Fluorescent Transformation Marker for *Drosophila* Transgenesis," *Dev. Genes Evol.* 210(12):623-629 (2000).
Horn et al., "A Versatile Vector Set for Animal Transgenesis," *Dev. Genes Evol.* 210(12):630-637 (2000).
Imamura et al., "Targeted Gene Expression using the *GAL4/UAS* System in the Silkworm *Bombyx mori*," *Genetics* 165(3):1329-1340 (2003).
Inoue et al., "Assembly of the Silk Fibroin Elementary Unit in Endoplasmic Reticulum and a Role of L-Chain for Protection of α1,2-Mannose Residues in N-Linked Oligosaccharide Chains of Fibrohexamerin/P25," *Eur. J. Biochem.* 271(2):356-366 (2004).
Tamura, "Transgenic Silkworm: Present Situation and Future," *J. Seric. Sci. Jpn.* 69(1):1-12 (2000).
Tamura, "Introduction of Useful Genes into Silkworm Eggs," *Kai Kisoikusyugaku Symposium Hokoku* 21:23-29 (2000).
Tamura, "Silkworms: Germ Line Transformation Technology and Production of Useful Substances," *Farming Japan* 37-3:20-25 (2003).
Tamura, "Production of New Silk Using Transgenic Silkworms," *Kobunshi.* 52(11):822-825 (2003).
Tamura, "Production of Useful Substance Using Transgenic Silkworm and Prospect of Future Utilization," *Bio Industry* 21(3):28-35 (2004).
Tamura et al., "Generation of Transgenic Silkworm Using Transposon Vectors," *Dai 7 Kai Konshu Kinou Kenkyukai Koen Toushi* 27:49-56 (1999).
Tamura et al., "Germline Transformation of the Silkworm *Bombyx mori* L. Using a *piggyBac* Transposon-Derived Vector," *Nat. Biotechnol.* 18(1):81-84 (2000).
Tamura et al., "Transgenic Silkworm Research in Japan: Recent Progress and Future," *Proceedings of Joint International Symposium of Insect COE Research Program and Insect Factory Research Project*, pp. 77-82 (2001).
Tamura et al., "Construction of Middle Silk Gland- Specific Gene Expression Method using *GAL4/UAS* System in the Silkworm," *Proceedings of the 74th Annual Meeting of the Japanese Society of Sericultural Science*, pp. 51 and 1-8, Abstract #213 (Mar. 29-30, 2004).
Thomas et al, "3×P3-EGFP Marker Facilitates Screening for Transgenic Silkworm *Bombyx mori* L. from the Embryonic Stage Onwards," *Insect Biochem. Mol. Biol.* 32(3):247-253 (2002).
Tomita et al., "Production of Transgenic Silkworms Bearing Human Collagen Genes," *Proceedings of the 24th Annual Meeting of Molecular Biology Society of Japan*, pp. 854, Abstract 4P-705 (Dec. 9-12, 2001).
Tomita et al., "Transgenic Silkworms Produce Recombinant Human Type III Procollagen in Cocoons," *Nat. Biotechnol.* 21(1):52-56 (2003).
Yamada et al., "Generation of Recombinant Silkworm That Produce Biologically Active Protein in Silk Filaments," *Brain Techno News* 97:6-10 (2003).
Berghammer et al., "A Universal Marker for Transgenic Insects," Nature 402:370-371 (1999).
Tomita et al., "A Germline Transgenic Silkworm that Secretes Recombinant Proteins in the Sericin Layer of Cocoon," Transgenic Res 16:449-465 (2007).

* cited by examiner

*Primary Examiner*—Anne Marie Wehbe
*Assistant Examiner*—Fereydoun G. Sajjadi
(74) *Attorney, Agent, or Firm*—Nixon Peabody LLP

(57) ABSTRACT

Transgenic silkworms comprising GFP whose expression is regulated by the sericin gene promoter were produced. Observation of the silk glands of the last instar larvae of the silkworms showed fluorescence only in the middle silk glands. GFP was secreted from middle silkgland cells from around the spinning stage, indicating that GFP moved into the gland lumen. Finally, GFP was spun into cocoon filaments, and cocoons containing large amounts of GFP were produced. Thus, by using the promoter region of the sericin gene, recombinant proteins can be produced in the middle silk glands. Furthermore, the recombinant proteins produced in the middle silk glands were readily secreted into the lumen of the middle silk glands.

9 Claims, 9 Drawing Sheets gaaattcttagctacatctagcccagactgtaagagtttcttaggagctttagaagttaaagaagtacct
ttgtgttgctgatccttctatatcatctggtcctagtaaaggtactctcttataatctccttcctaattc
cttacctgctatttatcgattgtaggtcgtcttggaaaccagtaccactgtacaaactcgcgccccatta
gtaacgtgatttgaacggccaaccaattgatgttttaatgcaattaatatcgtatctttaaccccaacgt
ggttctgcgttaactaagtgctcaccgctgtcaacagcaataaaaccattttttgaaataataacatcatt
acactaacatagtgagctagtcgcaaaatgtatgtagagagaaaacaaaccttctttgggtgttgagag
gaaatcgctggattagaactatcgtgaagaccattcactgatcctgtgtacttaaattcgcggattcagc
attaagcgccggatctcagttccatcgtaatcccagttaaagaggtgaaattagctatcacttcgatatc
tgttctgaaagcaatgttccacttgtaaaagcataagcggtcagaaacCTTGTTAACCAATAGAGCCAAA
TATAGTTAACACAATAGAAATTTATCCAAATATTATTCGTGTATTGTTTATAGCCTTTGTCAAGTCTTTT
ACAAGGCAAGATAATAAGTAATATTCCGTGATTGGACGTAACATTTCCCGGAAGATCCTTAGCCGATAAG
TCGAAGAGCCGCATGTGGCTAGAGAGACGCGGGTTTCCGACCACTGGCTTAGGCGCTTATTCCGCCATAA
TAGATGTACGTGTTCACAATTAGCACCCGAAATTCGTAATAGCTACGAGAAGTATCGAATATCAAAAATC
TATATATTAATACGTGAAGCAAAAACTTTGTATCCCTTTTTACGAAAATTGCGAGGACGGAGGAGTATGA
AATTTCCCACACTTATAGAGAATACAGAGAAGAAGTGCACAATGCTAATATTTTTTAAAATAATGCATA
AAAGATACTTTAAATCAATAAAGAAAACAGCACACACACTACATACCATGTATTTGACGCACACACGCAT
GTATACTATTTATTGTCAAACTTTTGTTCTTGACGTCTGTGTTCAAACTGAGAATAGATTAAATATTGTT
TGTCTTTATTAATATTTTTTAATAGTGTAGTCTTGGCGAAATTTGTGATTATAGAAGTATAAAATACAAT
CATAATAGTGTACAAACTTACAATTCCCAATTAATTATAGTCGAATTTCGACTACTGCGGGACCTCTAGT
ATTAATAATTCTCTTTAAAAAAAAACAGAGCATCAAATACTGTCACAAATGTCAAGCGG*GTCTCAACGAG*
*CCATGAATAAATTAGAAATCAATT* AATAACATAAAATAGGCAAACAAAATAAAACCATTTACATAGAGAA
CGTTTGTTGAACAAAAAC*AATAACTTGTATACATTGTTTGCACAAATGTTTG* AACCGAAAATTTATTACT
CTCTACGTAAGCTTGATCAAACTTCGTTTTCGTATAAAACGCGTTGGCCCAACCACTTTGGC<u>ATAGTCGT</u>
<u>CTTATCATCGGGTCTCTAAGGATCAAGCGATCcaaagaccgccaacATGcgtttcgttctgtgctgcact</u>
<u>ttgattgcgttg</u>gctgtgagtatcattgcttcgttatcaacaatgacgtatttactaagaacactcttag
atatgccttcaaattaaagctttcaaagctctgaagttcaccaaatgcgactgttttagcgtaagcattt
ctatcccccaacagccatttagcgactacccgaaaatcactcgatttaacttgggagtttctgcaattta
aaagttcacaggtcgtctccgattatacttttaaacgcttcgcgc ☐ : FIRST EXON
DOUBLE UNDERLINE: TATA SEQUENCE
ITALICS: REGIONS SA AND SC ASSOCIATED WITH GENE EXPRESSION
 CHARACTERISTICS

FIG. 1

SEQUENCE LISTING

<160> NUMBER OF SEQ ID NOS: 2

<210> SEQ ID NO 1
<211> LENGTH: 1935
<212> TYPE: DNA
<213> ORGANISM: Bombyx mori

<400> SEQUENCE: 1

```
gaaattctta gctacatcta gcccagactg taagagtttc ttaggagctt tagaagttaa      60
agaagtacct ttgtgttgct gatccttcta tatcatctgg tcctagtaaa ggtactctct     120
tataatctcc ttcctaattc cttacctgct atttatcgat tgtaggtcgt cttggaaacc     180
agtaccactg tacaaactcg cgccccatta gtaacgtgat ttgaacggcc aaccaattga     240
tgttttaatg caattaatat cgtatcttta accccaacgt ggttctgcgt taactaagtg     300
ctcaccgctg tcaacagcaa taaaaccatt tttgaaataa taacatcatt acactaacat     360
agtgagctag tcgcaaaatg tatgtagaga gaaaacaaac cttctttggg gtgttgagag     420
gaaatcgctg gattagaact atcgtgaaga ccattcactg atcctgtgta cttaaattcg     480
cggattcagc attaagcgcc ggatctcagt tccatcgtaa tcccagttaa agaggtgaaa     540
ttagctatca cttcgatatc tgttctgaaa gcaatgttcc acttgtaaaa gcataagcgg     600
tcagaaacct tgttaaccaa tagagccaaa tatagttaac acaatagaaa tttatccaaa     660
tattattcgt gtattgttta tagcctttgt caagtctttt acaaggcaag ataataagta     720
atattccgtg attggacgta acatttcccg gaagatcctt agccgataag tcgaagagcc     780
gcatgtggct agagagacgc gggtttccga ccactggctt aggcgcttat tccgccataa     840
tagatgtacg tgttcacaat tagcacccga aattcgtaat agctacgaga agtatcgaat     900
atcaaaaatc tatatattaa tacgtgaagc aaaaactttg tatcccttt tacgaaaatt       960 gcgaggacgg aggagtatga aatttcccac acttatagag aatacagaga agaagtgcac    1020
aatgctaata ttttttttaaa ataatgcata aaagatactt taaatcaata aagaaaacag    1080
cacacacact acataccatg tatttgacgc acacacgcat gtatactatt tattgtcaaa    1140
cttttgttct tgacgtctgt gttcaaactg agaatagatt aaatattgtt tgtctttatt    1200 aatattttt aatagtgtag tcttggcgaa atttgtgatt atagaagtat aaaatacaat    1260
cataatagtg tacaaactta caattcccaa ttaattatag tcgaatttcg actactgcgg    1320
gacctctagt attaataatt ctctttaaaa aaaaacagag catcaaatac tgtcacaaat    1380
gtcaagcggg tctcaacgag ccatgaataa attagaaatc aattaataac ataaaatagg    1440
caaacaaaat aaaaccattt acatagagaa cgtttgttga acaaaaacaa taacttgtat    1500
acattgtttg cacaaatgtt tgaaccgaaa atttattact ctctacgtaa gcttgatcaa    1560
acttcgtttt cgtataaaac gcgttggccc aaccactttg gcatagtcgt cttatcatcg    1620
ggtctctaag gatcaagcga tccaaagacc gccaacatgc gtttcgttct gtgctgcact    1680
ttgattgcgt tggctgtgag tatcattgct tcgttatcaa caatgacgta tttactaaga    1740
acactcttag atatgccttc aaattaaagc tttcaaagct ctgaagttca ccaaatgcga    1800
ctgttttagc gtaagcattt ctatccccca acagccattt agcgactacc cgaaaatcac    1860
```

```
tcgatttaac ttgggagttt ctgcaattta aaagttcaca ggtcgtctcc gattatactt    1920
ttaaacgctt cgcgc                                                     1935

<210> SEQ ID NO 2
<211> LENGTH: 2036
<212> TYPE: DNA
<213> ORGANISM: Bombyx mori

<400> SEQUENCE: 2
cagaatctac cacgatcgga aacgcgaccc actgagaaga tccggcgaga aactcagtga      60
gctgtgtcta tgggttaatt tactcgtcga ccctgttta ctgtttaggg cgacgtcgac     120
tgttaccatt cggtctacag gatcgagtgt gcattcttgt atcatcgttc tattatcacg    180
agtcattttg cgttttttcg gatccctgg aagtcgtcgt ggcctaagag ataagaagtc     240
cggtgcattc gtgttgagcg atgcacctgt gttcgaatcc taggcgggta ccaattttc     300 taatgaatta cgtacccaac aaatgttcac gattgccttc cacggtgaag gaataacatc    360
gtgcaataaa agtgaaaccc gcaaaatccg gtgcttttaa gcttttcaag caccggtcac    420
catcctcgtt gaactcatcg atctacaagc gatctaatct atagacccaa tccactaaga    480
tctcaccgga tcttctcagt ggttcgcatt ccagtggtag attcaattcg ctgctcttgc    540
tagggctagt gttagcaaat tccttcgggt taagcccgag agctcaccta tccgtccgcg    600
ctaagctgga aaagccccct aagctgtttt tttttttgtat agcctttatt gctaatacta    660
aacaataact aataatttta catacagtaa caaattgttt taacttaaat ctaatacatc    720
ggatttcccg gttcagtgat cagcgtgtcc tgtgacacat aggcctcttc cagctgcttt    780 cattttctc tattggtagc ttttcttgac cagattgtct ctccaatcat cttgatatcg     840
tctgtccatc ttctagcttg cctggctctt ttcctttaaa ccaggggtcg tgaattcaat    900
cctcacagga agccgggatt aggtgggaga atatagttcc gatgttttga atgctttata    960 tttctgtgg tcgaaaatga tactagagct acgcgtcgac aattgaatat tatgctaact    1020
accctctatt tattaaaaga cttttacgat tcatttcgca cagaaccaat cgactgggtt    1080
tagaggttta gcagtttgtt gaatgaactc gttttcatct tcacgattag aggatcccag    1140
gtgttaggta aaggatattc tagattgcag gagattttc ataaataatc acgcgatgga    1200
gcggtaatca gccaacatag tcgatcggca tcattattgg agaccaaaca acacttcagt    1260
tatccaagcg cgtcttaagt cgcattcgga taatcttgaa tagcctggaa gtgaattttt    1320
aaaaagtttg tctcgaacaa acatcaatta ctttgtaatt gaaccgaaaa aagaggataa    1380
acattattag cattcgttgt aatgaaatat aatgttgaca cagtttgacc gacgtgcact    1440 gtctttgtg gcaccggcta tataaaggtg gtctgtccgt tctgagccac acgagtcatc    1500
atgaagatcc catacgtctt gctgttcctt gtggtgagtt gctttcgttt ttgatatgct    1560
ggttcctcag gagtctgtac taatgcttct gttttattg tataaatgtg agcacttcac    1620
ggcctacgta accagctggt tacaatcacc gtccacgccg aaaaaatgag gcctgtatct    1680
aaattgtaac ataatttttg cacatttgat tctcatccca cgatttatt tatctttcat    1740 tcattttac tggtggtagg acgtcttgtg agtccgcacg tgcaccacct cacctatttc    1800
agccgtgaag cagtaatgcg cttcggtttg aagggtgggg cagccgttgt actttataaa    1860
cggagacctt agaactcatg tcccgagatg ggtggcagca tttacgttgc agatgtctat    1920
```

```
gggctccggt aaccacttaa catttttttt ttttctttt ttttttttt tatcacgcta    1980
cgttaattgg tcccgtgata agttcgtaaa gaacttgtgt tacaggtacc agataa      2036
```

METHODS FOR PRODUCING PROTEINS USING SILKWORM MIDDLE SILK GLAND-SPECIFIC GENE EXPRESSION SYSTEM

FIELD OF THE INVENTION

The present invention relates to methods for producing proteins using a silkworm middle silk-gland-specific gene expression system.

BACKGROUND OF THE INVENTION

Methods exist for producing recombinant proteins using *E. coli*, yeast, cultured mammalian cells, plants, animals, and such. These methods all have advantages and disadvantages, and thus appropriate methods are selected according to the characteristics and intended use of the proteins to be produced.

Methods using either the nuclear polyhedrosis viruses of lepidopteran insects or transgenic silkworms have been developed as recombinant protein production systems that use insects. The former uses a DNA-type virus as the vector. Recombinant viruses can be produced relatively easily, and can then infect the larvae of silkworms or other such insects. After infection, the viruses grow in the insect individuals, resulting in recombinant protein synthesis from the genes introduced into the virus. In this method, as the virus-infected larvae die a few days later, the proteins are collected from the body fluid of the silkworm just before death, and are purified. In most cases, the amount of protein that can be produced is 1 mg or less per 1 mL of body fluid. Therefore, the purification procedure of this method is highly laborious.

Methods using recombinant silkworms utilize the silk gland, which is a unique organ of silkworms. The silk gland can be divided into the anterior, middle, and posterior regions; each has a different function. More specifically, the anterior silk gland almost has no protein-producing function, whereas 75% of the cocoon filament protein is produced in the posterior silk gland, and the remaining 25% is produced in the middle silk gland. Fibroin is produced in the posterior silk gland, and sericin is produced in the middle silk gland. Previous studies have produced posterior silk-gland-specific gene expression systems, but there are no previous successful examples of recombinant protein production from the middle silk gland.

SUMMARY OF THE INVENTION

The present invention was made in view of such a situation. An objective of this invention is to provide methods for producing recombinant proteins from the silkworm middle silk gland.

The present inventors conducted extensive studies to solve the above-mentioned problems. Approximately 1 kb of the region upstream of the sericin 1 gene was used as a promoter region, which was inserted upstream of the GAL4 gene. Then, this fused gene was inserted into a plasmid vector for producing transgenic silkworms. Production of transgenic silkworms was carried out by the method of Tamura et al. (2000). The transgenic silkworms thus obtained were crossed with a UASGFP homozygous silkworm strain produced by the method of Imamura et al. (2003). The UASGFP homozygous silkworm strain carries a green fluorescent protein gene as a reporter downstream of the GAL4 target sequence, UAS. The present inventors examined the silk glands of the last instar larvae of transgenic silkworms obtained by crossing, and found that fluorescence was limited to the middle silk glands of this strain. Furthermore, GFP was secreted from the middle silk gland cells, beginning at the spinning stage of silkworm development. This indicates that GFP was transferred into the gland lumen. Ultimately, GFP was spun as cocoon filaments, resulting in cocoons containing large amounts of GFP. As described above, the GFP gene used in this study does not comprise a signal sequence for secretion, yet the resultant GFP was found to be secreted in large amounts into the middle silk gland lumen, and transferred into the cocoon filaments.

More specifically, the present invention relates to methods for producing recombinant proteins from the silkworm middle silk gland, and provides [1] to [25] as described below.

[1] A method for producing an arbitrary protein, wherein the method comprises the steps of:
(a) producing a transgenic silkworm comprising
a promoter of a DNA encoding a protein that is expressed in a middle silk-gland-specific manner; and
a DNA encoding an arbitrary protein whose expression is regulated directly or indirectly by the promoter,
wherein the transgenic silkworm secretes the arbitrary protein into cocoon filaments; and
(b) recovering the arbitrary protein from the produced transgenic silkworm.

[2] The method of [1], wherein the transgenic silkworm comprises the DNAs of (i) and (ii):
(i) a DNA encoding a transcriptional regulator that is operably linked downstream of a promoter of a DNA encoding a protein that is expressed in a middle silk-gland-specific manner; and
(ii) a DNA encoding an arbitrary protein that is operably linked downstream of a target promoter of the transcriptional regulator.

[3] The method of [2], wherein the transcriptional regulator is GAL4, and the target promoter is UAS.

[4] The method of [1], wherein the transgenic silkworm is produced by crossing the transgenic silkworms of (i) and (ii):
(i) a transgenic silkworm comprising a DNA encoding a transcriptional regulator that is operably linked downstream of a promoter of a DNA encoding a protein that is expressed in a middle silk-gland-specific manner; and
(ii) a transgenic silkworm comprising a DNA encoding an arbitrary protein that is operably linked downstream of a target promoter of the transcriptional regulator.

[5] The method of [4], wherein the transcriptional regulator is GAL4, and the target promoter is UAS.

[6] A method for producing a transgenic silkworm that secretes an arbitrary protein into the cocoon filaments, wherein the method comprises the step of producing a silkworm egg comprising
a promoter of a DNA encoding a protein that is expressed in a middle silk-gland-specific manner; and
a DNA encoding an arbitrary protein whose expression is regulated directly or indirectly by the promoter.

[7] The method of [6], wherein the transgenic silkworm comprises the DNAs of (i) and (ii):
(i) a DNA encoding a transcriptional regulator that is operably linked downstream of a promoter of a DNA encoding a protein that is expressed in a middle silk-gland-specific manner; and
(ii) a DNA encoding an arbitrary protein that is operably linked downstream of a target promoter of the transcriptional regulator.

[8] The method of [7], wherein the transcriptional regulator is GAL4, and the target promoter is UAS.

[9] The method of [6], wherein the transgenic silkworm is produced by crossing the transgenic silkworms of (i) and (ii):

(i) a transgenic silkworm comprising a DNA encoding a transcriptional regulator that is operably linked downstream of a promoter of a DNA encoding a protein that is expressed in a middle silk-gland-specific manner; and (ii) a transgenic silkworm comprising a DNA encoding an arbitrary protein that is operably linked downstream of a target promoter of the transcriptional regulator.

[10] The method of [9], wherein the transcriptional regulator is GAL4, and the target promoter is UAS.

[11] The method of any one of [1] to [10], wherein the promoter of a DNA encoding a protein that is expressed in a middle silk-gland-specific manner is a promoter of a DNA encoding either the sericin 1 protein or the sericin 2 protein.

[12] The method of any one of [1] to [10], wherein the promoter of a DNA encoding a protein that is expressed in a middle silk-gland-specific manner is (a) or (b):

(a) a DNA comprising the nucleotide sequence of SEQ ID NO: 1 or 2; or (b) a DNA comprising a nucleotide sequence with one or more nucleotide substitutions, deletions, additions, and/or insertions in the nucleotide sequence of SEQ ID NO: 1 or 2.

[13] The method of any one of [1] to [10], wherein the arbitrary protein does not comprise a signal for secretion from silk gland cells to silk gland lumen.

[14] A transgenic silkworm comprising
a promoter of a DNA encoding a protein that is expressed in a middle silk-gland-specific manner; and
a DNA encoding an arbitrary protein whose expression is regulated directly or indirectly by the promoter,
wherein the transgenic silkworm secretes the arbitrary protein into cocoon filaments.

[15] The transgenic silkworm of [14], which comprises the DNAs of (i) and (ii):

(i) a DNA encoding a transcriptional regulator that is operably linked downstream of a promoter of a DNA encoding a protein that is expressed in a middle silk-gland-specific manner; and (ii) a DNA encoding an arbitrary protein that is operably linked downstream of a target promoter of the transcriptional regulator.

[16] The transgenic silkworm of [15], wherein the transcriptional regulator is GAL4, and the target promoter is UAS.

[17] The transgenic silkworm of [14], which is produced by crossing the transgenic silkworms of (i) and (ii):

(i) a transgenic silkworm comprising a DNA encoding a transcriptional regulator that is operably linked downstream of a promoter of a DNA encoding a protein that is expressed in a middle silk-gland-specific manner; and (ii) a transgenic silkworm comprising a DNA encoding an arbitrary protein that is operably linked downstream of a target promoter of the transcriptional regulator.

[18] The transgenic silkworm of [17], wherein the transcriptional regulator is GAL4, and the target promoter is UAS.

[19] The transgenic silkworm of any one of [14] to [18], wherein the promoter of a DNA encoding a protein that is expressed in a middle silk-gland-specific manner is a promoter of a DNA encoding either the sericin 1 protein or the sericin 2 protein.

[20] The transgenic silkworm of any one of [14] to [18], wherein the promoter of a DNA encoding a protein that is expressed in a middle silk-gland-specific manner is (a) or (b):

(a) a DNA comprising the nucleotide sequence of SEQ ID NO: 1 or 2; or (b) a DNA comprising a nucleotide sequence with one or more nucleotide substitutions, deletions, additions, and/or insertions in the nucleotide sequence of SEQ ID NO: 1 or 2.

[21] The transgenic silkworm of any one of [14] to [18], wherein the arbitrary protein does not comprise a signal for secretion from silk gland cells to silk gland lumen.

[22] A transgenic silkworm comprising a DNA encoding a transcriptional regulator that is operably linked downstream of a promoter of a DNA encoding a protein that is expressed in a middle silk-gland-specific manner.

[23] The transgenic silkworm of [22], wherein the transcriptional regulator is GAL4.

[24] The transgenic silkworm of [22] or [23], wherein the promoter of a DNA encoding a protein that is expressed in a middle silk-gland-specific manner is a promoter of a DNA encoding either the sericin 1 protein or the sericin 2 protein.

[25] The transgenic silkworm of [22] or [23], wherein the promoter of a DNA encoding a protein that is expressed in a middle silk-gland-specific manner is (a) or (b):

(a) a DNA comprising the nucleotide sequence of SEQ ID NO: 1 or 2; or (b) a DNA comprising a nucleotide sequence with one or more nucleotide substitutions, deletions, additions, and/or insertions in the nucleotide sequence of SEQ ID NO: 1 or 2.

BRIEF DESCRIPTION OF THE DRAWINGS

FIG. 1 shows the nucleotide sequence of the upstream region of the sericin 1 gene (SEQ ID NO:1) and the region that was used as the promoter. The first exon is shown in the boxed region. SA and SC regions considered to be involved in transcriptional regulation are indicated by single underlines, and the TATA region is indicated by a double line.

DETAILED DESCRIPTION OF THE INVENTION

Figure 2:
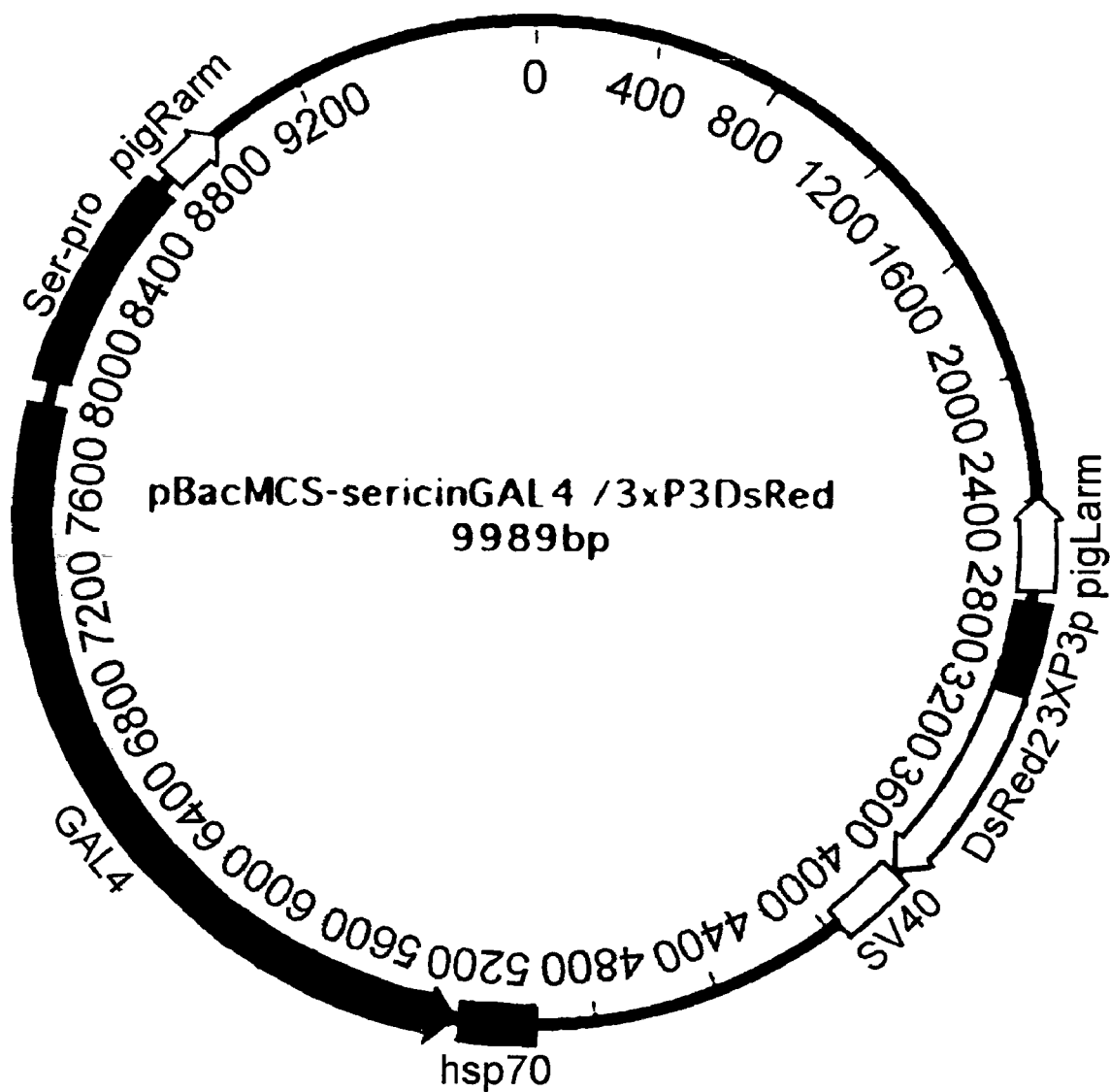
FIG. 2 shows the structure of the vector for producing transgenic silkworms, which uses the upstream region of the sericin gene. Serpro, sericin gene promoter region; GAL4, GAL4 gene; hsp70, poly (A) region of *Drosophila* Hsp70gene; pigLarm, the left terminus of piggyBac transposon; pigRarm, the right terminus of piggyBac transposon; 3XP3, an artificial promoter that is specifically expressed in eyes; DsRed, a gene encoding DsRed; and SV40, poly(A) signal of SV40.

The present invention provides methods for producing discretionary proteins, wherein the methods comprise the steps of:

(a) producing a transgenic silkworm comprising a promoter of a DNA encoding a protein that is expressed in a middle silk-gland-specific manner; and a DNA encoding the arbitrary protein whose expression is regulated directly or indirectly by the promoter, wherein the transgenic silkworm secretes the arbitrary protein into cocoon filaments; and (b) recovering the arbitrary protein from the produced transgenic silkworm.

In the first step of producing transgenic silkworms of this invention, silkworm eggs are produced that comprise a promoter of a DNA encoding a protein that is expressed in a middle silk-gland-specific manner; and a DNA encoding the arbitrary protein whose expression is regulated directly or indirectly by the promoter. Next, transgenic silkworms that express the arbitrary protein are selected from the silkworms that hatched from the produced silkworm eggs.

In this invention, transgenic silkworms are selected, for example, by using selection markers. Markers that are conventionally used by those skilled in the art, such as the fluorescent proteins CFP (cyan fluorescent protein), GFP (green fluorescent protein), YFP (yellow fluorescent protein), DsRed (Discosoma red fluorescent protein), and others, can be used as selection markers of this invention. The use of these markers enables the detection of transgenic silkworms simply by observation using a fluorescence stereoscopic microscope. Furthermore, since each of the fluorescent colors emitted is different, a plurality of markers can be used simultaneously.

Examples of methods for recovering discretionary proteins from the produced transgenic silkworms include methods for recovering discretionary proteins from the cocoons spun by the transgenic silkworms. Methods well known to those skilled in the art, such as the method for recovering proteins by dissolving the cocoons in 60% LiSCN, and then dialyzing in 20 mM Tris and 5 M urea (Inoue, S., Tsuda, H., Tanaka, H., Magoshi, Y., and Mizuno (2001) Sericologia 4, 157-163) may be used as the recovering method. Other feasible methods for recovering proteins include, for example, methods using surfactants, and methods comprising the step of dissolving in aqueous solution.

Examples of the silkworm eggs comprising a promoter of a DNA encoding a protein that is expressed in a middle silk-gland-specific manner, and a DNA encoding an arbitrary protein whose expression is regulated indirectly by the promoter, include silkworm eggs comprising: (i) a DNA encoding a transcriptional regulator is operably linked downstream of a promoter of a DNA encoding a protein that is expressed in a middle silk-gland-specific manner; and (ii) a DNA encoding an arbitrary protein that is operably linked downstream of a target promoter of the transcriptional regulator.

A variety of methods can be selected as methods for producing such silkworm eggs. For example, the above-described DNAs of (i) and (ii) can be introduced into separate silkworm eggs. Silkworm eggs comprising both DNAs can be obtained by producing the transgenic silkworms from the silkworm eggs to which the individual DNAs had been introduced, and then crossing the transgenic silkworms with each other. In this case, the expression tissue, timing, and level can be adjusted by the transcriptional regulator. Therefore, this method is advantageous in that by crossing with a strain to which a gene to be expressed has been introduced, the expression tissue, timing, level, and such can be altered without having to generate many strains. Experiments can still be carried out despite the infertility that may be caused by expression of the gene of interest. An additional advantage is the increased level of protein produced from the introduced gene compared to the use of a single promoter. Alternatively, silkworm eggs comprising the DNAs of (i) and (ii) can be obtained by obtaining eggs ovi positioned by a transgenic silkworm to which one of the DNAs has been introduced, and then artificially introducing the other DNA into the eggs. Silkworm eggs comprising both DNAs can also be obtained by introducing the above-described DNAs of (i) and (ii) into the same egg (Imamura, M., Nakai, J., Inoue, S., Quan, G.-X., Kanda, T. and Tamura, T. (2003) Targeted gene expression using the GAL4/UAS system in the silkworm Bombyx mori. Fourth International Workshop on Transgenesis and Genomics of Invertegrate Organisms, Asilomar, p. 53).

Examples of the silkworm eggs comprising a promoter of a DNA encoding a protein that is expressed in a middle silk-gland-specific manner, and a DNA encoding an arbitrary protein whose expression is regulated directly by the promoter, include silkworm eggs comprising a DNA encoding an arbitrary protein that is operably linked downstream of a promoter of a DNA encoding a protein that is expressed in a middle silk-gland-specific manner. Such silkworm eggs can be produced by introducing into eggs, the DNA encoding an arbitrary protein that is operably linked downstream of a promoter of the DNA encoding a protein that is expressed in a middle silk-gland-specific manner.

The phrase "operably linked" means that a promoter and a DNA are linked, so that expression of the DNA located downstream of the promoter is induced by the binding of a transcriptional regulator to the promoter. Therefore, even if the DNA is linked to a second gene and a fusion protein is produced from the linked genes, as long as the expression of the fusion protein is induced by the binding of the transcriptional regulator to the promoter, this DNA can be considered to be "operably linked" as described above.

Examples of the combination of the transcriptional regulator and target sequence include GAL4 and UAS, and TetR and TRE. By using GAL4 and UAS, or TetR and TRE, the expression site, expression timing, and expression level of the gene of interest can be regulated precisely, and the gene can be easily expressed in many tissues. Furthermore, a strain can be established even if the gene to be expressed is a lethal gene.

Examples of the promoters of this invention, that is, promoters of DNAs encoding proteins that are expressed in a middle silk-gland-specific manner, are the promoters of the DNAs encoding either the sericin 1 or sericin 2 proteins. The promoters of the DNAs encoding the sericin 1 and sericin 2 proteins include, for example, DNAs comprising the nucleotide sequences of SEQ ID NO: 1 and 2, respectively. Examples of the DNAs comprising the nucleotide sequence of SEQ ID NO: 1 or 2 include DNAs comprising the nucleotide sequence of SEQ ID NO: 1 or 2, and DNAs comprising the DNAs consisting of the nucleotide sequence of SEQ ID NO: 1 or 2 and the upstream and downstream regions thereof but are not limited thereto. The upstream and downstream regions of the DNAs comprising the nucleotide sequence of SEQ ID NO: 1 or 2 are disclosed in the literature (Okamoto, H., Ishikawa, E. and Suzuki, Y. (1982) Structural analysis of sericin genes. Homologies with fibroin gene in the 5' flanking nucleotide sequences. J Biol Chem, 257, 15192-15199; Garel, A., Deleage, G. and Prudhomme, J. C. (1997) Structure and organization of the Bombyx mori sericin 1 gene and of the sericins 1 deduced from the sequence of the Ser 1 B cDNA. Insect Biochem Mol Biol, 27, 469-477; Michaille, J. J., Garel, A. and Prudhomme, J. C. (1990) Cloning and characterization of the highly polymorphic Ser2 gene of *Bombyx mori*. Gene, 86, 177-184).

Furthermore, in this invention, an example of the promoter of a DNA encoding a protein that is expressed in a middle silk-gland-specific manner, may be a DNA that is structurally similar to the DNAs comprising the nucleotide sequence of SEQ ID NO: 1 or 2, and that has promoter activity equivalent to or improved over the activities of the DNAs comprising the nucleotide sequence of SEQ ID NO: 1 or 2. Such a DNA may be, for example, a DNA comprising the nucleotide sequence of SEQ ID NO: 1 or 2, wherein one or more nucleotides are replaced, deleted, added, and/or inserted. This DNA can be produced by methods such as hybridization techniques, polymerase chain reaction (PCR) techniques, site-directed mutagenesis, and DNA synthesis. Whether the prepared DNAs have promoter activity can be examined by those skilled in the art, for example, using well-known reporter assays with reporter genes.

The reporter genes are not particularly limited as long as their expression is detectable, and include the CAT gene, lacZ gene, luciferase gene, β-glucuronidase gene (GUS), and GFP gene, which are generally used by those skilled in the art. The expression level of the reporter genes can be measured according to the type of the reporter genes by methods well known to those skilled in the art. For example, when the reporter gene is the CAT gene, the expression level of the reporter gene can be measured by detecting the acetylation of chloramphenicol catalyzed by the gene product. The expression level of the reporter gene can be measured by:

detecting the color development of pigment compound as a result of the catalytic action of the gene expression product when the reporter gene is the lacZ gene;

detecting the fluorescence of fluorescent compound as a result of the catalytic action of the gene expression product when the reporter gene is the luciferase gene;

detecting the luminescence of Glucuron (ICN) or the color development of 5-bromo-4-chloro-3-indolyl-β-glucuronide (X-Gluc) as a result of the catalytic action of the gene expression product when the reporter gene is the β-glucuronidase gene (GUS); and detecting the fluorescence of the GFP protein when the reporter gene is the GFP gene.

Preferably, the arbitrary proteins of the present invention do not undergo irreversible denaturation in the silk. Examples of the arbitrary proteins include proteins that do not comprise a signal for secretion from silk gland cells to the silk gland lumen, and proteins that are nonfibrous.

DNAs can be introduced into silkworm eggs, for example, according to the method for injecting transposons as a vector into silkworm eggs in the early developmental stage (Tamura, T., Thibert, C., Royer, C., Kanda, T., Abraham, E., Kamba, M., Komoto, N., Thomas, J.-L., Mauchamp, B., Chavancy, G. Shirk, P., Fraser, M., Prudhomme, J.-C. and Couble, P., 2000, Nature Biotechnology 18, 81-84).

For example, a vector in which the above-described DNA is inserted into the inverted terminal repeat of the transposon (Handler A M, McCombs S D, Fraser M J, Saul S H. (1998))) Proc. Natl. Acad. Sci. U.S.A. 95(13):7520-5) is introduced into silkworm eggs along with a vector comprising a DNA encoding a transposon transferase (helper vector). An example of a helper vector is pHA3PIG (Tamura, T., Thibert, C., Royer, C., Kanda, T., Abraham, E., Kamba, M., Komoto, N., Thomas, J.-L., Mauchamp, B., Chavancy, G. Shirk, P., Fraser, M., Prudhomme, J.-C. and Couble, P., 2000, Nature Biotechnology 18, 81-84), but the present invention is not limited thereto.

An example of the transposons of the present invention is preferably piggyBac, but is not limited thereto. Transposons such as mariner and minos may be used (Shimizu, K., Kamba, M., Sonobe, H., Kanda, T., Klinakis, A. G., Savakis, C. and Tamura, T. (2000) Insect Mol. Biol., 9, 277-281; Wang W, Swevers L, Iatrou K. (2000) Insect Mol Biol 9(2):145-55).

In the present invention, transgenic silkworms can also be produced using baculovirus vectors (Yamao, M., N. Katayama, H. Nakazawa, M. Yamakawa, Y. Hayashi et al., 1999, Genes Dev 13: 511-516).

The silkworms of this invention are not particularly limited. However, in order to produce large amounts of the arbitrary protein, it is preferable to use silkworms in which the production of proteins constituting the silk is suppressed by mutations in regions (including the coding regions, promoter regions, and untranslated regions) of the genes that encode proteins, such as the fibroin protein, which constitute the silk thread. Examples of such silkworms may include mutant silkworm strains, in which the production of proteins constituting the silk thread is suppressed by mutations in the genetic region encoding these proteins; and preferably include exarate pupae of silkworms, in which the production of proteins constituting the silk thread are suppressed by the mutations, or more preferably include the silkworm strain Nd-$s^D$. However, any silkworms are appropriate as long as production of proteins constituting the silk thread is suppressed, regardless of whether the production of proteins constituting the silk thread is artificially suppressed or depends on naturally occurring mutations. Such silkworms are well known to those skilled in the art as "sericin silkworms." The use of sericin silkworms facilitates purification of proteins synthesized from the arbitrary genes introduced into the chromosome.

Silkworms having the characteristic of ovipositioning nondiapausing eggs, as well as silkworms having the characteristic of ovipositioning diapausing eggs (for example, silkworm varieties for practical use include Gunma, 200, Shunrei, Shogetsu, Kinshu, Showa, and such) may be used as the silkworms of the present invention. Herein, the term "diapausing eggs" refers to eggs in which embryogenesis after oviposition is transiently stopped, and the term "nondiapausing eggs" refers to eggs in which embryogenesis after oviposition does not stop, and leads to larval hatching.

When silkworms having the characteristic of ovipositioning diapausing eggs are used, DNAs are introduced into the nondiapausing eggs after they have been laid. For example, the silkworm variety Gunma can be induced to oviposition nondiapausing eggs, by methods of culturing diapausing eggs at 15° C. to 21° C. to induce adults that were hatched from the diapausing eggs to oviposition nondiapausing eggs, preferably by methods of culturing diapausing eggs at 16° C. to 20° C. to induce adults that were hatched from the diapausing eggs to oviposition nondiapausing eggs, more preferably by methods of culturing diapausing eggs at 18° C. to induce adults that were hatched from the diapausing eggs to oviposition nondiapausing eggs, and most preferably by methods of culturing diapausing eggs at 18° C. and rearing under continuous light at the larval stage to induce adults that were hatched from the diapausing eggs to oviposition nondiapausing eggs. The silkworm variety 200 can be induced to oviposition nondiapausing eggs, by methods of culturing diapausing eggs at 15° C. to 21° C. to induce adults that were hatched from the diapausing eggs to oviposition nondiapausing eggs, preferably by methods of culturing diapausing eggs at 16° C. to 20° C. to induce adults that were hatched from the diapausing eggs to oviposition nondiapausing eggs, more preferably by methods of culturing diapausing eggs at 18° C to induce adults that were hatched from the diapausing eggs to oviposition nondiapausing eggs, or by methods of rearing diapausing eggs under continuous light at the larval stage to induce adults that were hatched from the diapausing eggs to oviposition nondiapausing eggs; and most preferably by methods of culturing diapausing eggs at 25° C. and rearing under continuous light at the larval stage to induce adults that were hatched from the diapausing eggs to oviposition nondiapausing eggs.

The eggs can be cultured in an incubator at 18° C. to 25° C. or in a constant temperature room. Larvae can be reared on an artificial diet in a breeding room at 20° C. to 29° C.

In the present invention, the term "day length conditions" means the daily light and dark cycle for culturing eggs or rearing larvae. Such conditions include light conditions and dark conditions. In particular, a condition of continuous light refers to a condition of 24 hours of light and no darkness. The day length conditions can be changed according to the breed.

The diapausing eggs of the present invention as described above can be cultured according to methods for culturing silkworm eggs common to those skilled in the art. For example, culturing can be performed using the method described in "Monbusho (Ministry of Education) (1978) Sanshu Seizo (Production of silkworm varieties) p. 193, Jikkyo Shuppan, Tokyo." The silkworm larvae of the present invention can be reared by methods well known to those skilled in the art. For example, silkworm larvae are reared according to the method described in "Monbusho (Ministry of Education) (1978) Sanshu Seizo (Production of silkworm varieties) p. 193, Jikkyo Shuppan, Tokyo."

In the present invention, whether the ovipositioned eggs are nondiapausing eggs can be determined from the color of the eggs. It is generally known that diapausing eggs are dark brown in color and nondiapausing eggs are pale yellow. Therefore, in the present invention, the ovipositioned eggs are determined to be nondiapausing eggs if the color is not dark brown, and preferably if the color is pale yellow.

Hereinbelow, examples of methods for introducing DNA into silkworm eggs will be specifically described, but methods of the present invention for introducing DNA into silkworm eggs are not limited thereto. For example, DNAs can be introduced directly into silkworm eggs using a DNA injection tube. In a preferred embodiment, a hole is made physically or chemically in an eggshell in advance, and then the DNAs are introduced through this hole. In this case, the DNA injection tube can be inserted into the egg through the hole by adjusting the insertion angle to be nearly perpendicular to the ventral surface of the egg.

In the present invention, examples of the methods for physically making a hole in the eggshell include hole making methods that use needles, microlasers, or such. Preferably, a hole can be made in an eggshell by methods using needles. The material, the strength, and such of the needles are not particularly limited, as long as the needles can make a hole in the silkworm eggshells. The needles in the present invention ordinarily refer to rod-shaped needles having a sharp tip, but are not limited to this form. As long as the needles can make a hole in an eggshell, there are no particular limitations on their overall shape. For example, a pyramid-shaped object with a sharp tip, and a cone-shaped object with a sharp tip are also included in the "needles" of this invention. In this invention, tungsten needles can be preferably used. The needles of the present invention have enough thickness (diameter) to make holes that allow the capillary, as described below, to pass through. The needle thickness is generally 2 to 20 μm, and preferably 5 to 10 μm. On the other hand, examples of methods for chemically making a hole in an eggshell include hole making methods that use chemical agents (for example, hypochlorous acid) or such.

In the present invention, the position of the hole is not particularly limited as long as a DNA injection tube can be inserted through the hole at an insertion angle that is nearly perpendicular to the ventral surface of the egg. The ventral side and its opposite side of the egg are preferable; the ventral side is more preferable; and the central portion of the ventral side slightly towards the posterior end is even more preferable.

In the present invention, the phrase "nearly perpendicular" means 70° to 120°, and preferably 80° to 90° to the ventral surface of the egg. In this invention, the phrase "the position where germ cells will be developed in the future" usually refers to a position close to the egg surface at the ventral side of the egg (normally 0.01 mm to 0.05 mm beneath the egg surface), and preferably a position near the egg surface at the center of the ventral side of the egg, slightly towards the posterior end.

In the present invention, the material, strength, internal diameter, and such of tubes for injecting DNAs are not particularly limited. However, when a hole is made physically or chemically in the eggshell before insertion of the DNA injection tube, the tube preferably has enough thickness (external diameter) to pass through the opened hole. In this invention, examples of the DNA injection tube include a glass capillary.

In a preferred embodiment of the DNA transfer methods of the present invention, an all-in-one manipulator equipped with a DNA injection tube and a needle is used to perform the steps of: physically or chemically opening a hole in a silkworm egg; inserting the DNA injection tube through the hole into the egg at an insertion angle nearly perpendicular to the ventral surface of the egg; and injecting DNAs. The present invention is preferably carried out using an apparatus comprising the manipulator as one of the components.

Such an apparatus consists of a dissecting microscope, an illuminator, a movable stage, a coarse manipulator fixed to the microscope with a metal fitting, a micromanipulator attached to this manipulator, and an injector that adjusts the air pressure for DNA injection. The pressure applied by the injector is provided from a nitrogen tank, and a pressure switch can be operated using a foot switch. Injection is performed on eggs immobilized onto a substrate such as a glass slide and the position of the eggs is adjusted using a movable stage. The glass capillary of the micromanipulator is connected to and operated by an operating portion connected to four tubes. Specifically, the position of the tungsten needle relative to an egg is adjusted using the coarse manipulator, and then a hole is made by shifting the egg in the horizontal direction using the stage lever. Next, the lever of the micromanipulator operating portion guides the tip of the glass capillary to the position of the hole, and the capillary is inserted into the egg using the stage lever. In this case, the glass capillary must be inserted perpendicularly to the ventral surface of the egg. The foot switch is then operated to inject DNAs, and the lever is operated to draw out the capillary from the egg. The opened hole is closed using instant adhesive or similar, and the egg is protected in an incubator at constant temperature and constant humidity. The apparatus used in this invention is preferably the apparatus described in JP Patent No. 1654050, or a modified version of this apparatus.

Furthermore, in an embodiment of the present invention, the silkworm eggs to which DNAs are introduced are preferably immobilized onto a substrate. Examples of the substrate used in this invention include a glass slide and plastic sheet, but are not particularly limited thereto. In this embodiment of the present invention, the eggs are immobilized preferably after their direction is properly arranged, so that the DNAs can be injected precisely to the position in the silkworm egg where germ cells will be developed in the future. Furthermore, in this embodiment, the number of silkworm eggs immobilized onto the substrate is not particularly limited. When multiple silkworm eggs are used, it is preferable that the silkworm eggs are unidirectionally immobilized onto the substrate in a dorsoventral direction. The immobilization of the silkworm eggs to a substrate according to this invention can be performed, for example, by inducing oviposition on commercially available cards (various egg cards) precoated with water-soluble glue, detaching eggs by adding water to the cards, and aligning the wet eggs on a substrate to be air-dried. The eggs are preferably immobilized onto a glass slide after properly arranging the direction of the eggs. Immobilization of the eggs onto the substrate can be also accomplished by using a double-sided adhesive tape, adhesive, or such.

To confirm whether the DNAs have been successfully introduced into the silkworm eggs, for example, a method for re-extracting and analyzing injected DNAs from the eggs (Nagaraju, J., Kanda, T., Yukuhiro, K., Chavancy, G, Tamura, T. and Couble, P. (1996) Attempt of transgenesis of the silkworm (Bombyx mori L) by egg-injection of foreign DNA. Appl. Entomol. Zool., 31, 589-598), or a method for observing the gene expression of injected DNAs in the eggs (Tamura, T., Kanda, T., Takiya, S., Okano, K. and Maekawa, H. (1990) Transient expression of chimeric CAT genes injected into early embryos of the domesticated silkworm, Bombyx mori. Jpn. J. Genet., 65, 401-410) can be used.

Furthermore, pharmaceutical compositions can be prepared by combining pharmaceutically acceptable carriers with the proteins recovered by the methods of the present invention. Examples of the carriers include surfactants, fillers, coloring agents, flavoring agents, preservatives, stabilizers, buffers, suspending agents, isotonizing agents, binding agents, disintegrators, lubricants, fluidizing agents, and corrigents, but are not limited thereto. Other conventional carriers can be also used appropriately. Specifically, light anhydrous silicic acid, lactose, crystalline cellulose, mannitol, starch, calcium carmellose, sodium carmellose, hydroxypropylcellulose, hydroxypropylmethylcellulose, polyvinylacetal diethylaminoacetate, polyvinylpyrrolidone, gelatin, middle-chain fatty acid triglyceride, polyoxyethylene hydrogenated castor oil 60, sucrose, carboxymethylcellulose, corn starch, inorganic salts, and such can be used.

Furthermore, the present invention provides transgenic silkworms comprising a promoter of a DNA encoding a protein that is expressed in a middle silk-gland-specific manner and a DNA encoding an arbitrary protein whose expression is regulated directly or indirectly by the promoter, wherein the transgenic silkworm secretes the arbitrary protein into cocoon filaments. There are no limitations as to the stage of the transgenic silkworms of the present invention, and they may be in the egg stage. By using the transgenic silkworms of the present invention, large amounts of the protein of interest can be produced.

The preferable transgenic silkworms of the present invention are: those comprising (i) a DNA encoding a transcriptional regulator that is operably linked downstream of a promoter of a DNA encoding a protein that is expressed in a middle silk-gland-specific manner; and
(ii) a DNA encoding an arbitrary protein that is operably linked downstream of a target promoter of the transcriptional regulator; and
those comprising a DNA in which a DNA encoding an arbitrary protein is operably linked downstream of a promoter of a DNA encoding a protein that is expressed in a middle silk-gland-specific manner.

Furthermore, the present invention provides transgenic silkworms comprising the DNA of (i). Such silkworms can be used to produce transgenic silkworms comprising the DNAs of (i) and (ii), and eggs thereof.

The present invention also provides cocoons of the transgenic silkworms of this invention. Such cocoons are useful as they comprise a large amount of the protein of interest. The present invention also provides silk produced from the cocoons, in which the silk thread comprises the arbitrary protein. Silk fabric comprising the silk thread of the present invention, such as silk fabric comprising antibacterial silk thread, can be produced using known methods. The present invention also provides such silk fabric.

In addition, the present invention provides DNAs to be used in the methods of this invention. Such DNAs comprise: (a) a DNA encoding a transcriptional regulator operably linked downstream of a promoter of a DNA encoding sericin; (b) a DNA encoding an arbitrary protein operably linked downstream of the target promoter of the transcriptional regulator; and (c) a DNA in which a DNA encoding an arbitrary protein is operably linked downstream of a promoter of a DNA encoding sericin. Such DNAs may be provided as a kit comprising a combination of these DNAs. This invention also provides vectors in which the DNAs of (a) to (c) are inserted into the inverted terminal repeat of a transposon. Furthermore, this invention provides kits comprising the vector, as well as a helper vector comprising a DNA encoding the transposase.

Fibroin synthesized in the posterior silk glands accounts for 75% of the cocoon filament protein level in a silkworm, whereas sericin synthesized in the middle silk glands accounts for approximately 25%. Accordingly, the relative production level of sericin is below that of fibroin. The system for producing recombinant proteins in the middle silk gland is considered more suitable for producing nonfibrous proteins than that of the posterior silk gland, in view of the following reasons. Fibroin is a fibrous protein that is extremely insoluble in water. Furthermore, the secretion of proteins synthesized in the posterior silk gland (where fibroin is synthesized) into the lumen is very strictly regulated, and requires a portion of the fibroin H-chain or L-chain sequence. Thus, this system is disadvantageous in that recombinant proteins produced therein must be produced as fusion proteins with these unnecessary amino acid sequences. The system of the present invention is advantageous as a protein production system because the sericin protein is far more water-soluble than fibroin and is secreted into the gland lumen even in the absence of a special signal sequence, as demonstrated by this experiment.

EXAMPLES

Hereinbelow, the present invention will be specifically described using Examples, but it is not to be construed as being limited thereto.

Example 1

1. Materials and Methods

Silkworms of the nondiapausing egg strain, w1-pnd, were used for producing transgenic silkworms. In a breeding room used exclusively for transgenic silkworms, the silkworms were reared on an artificial diet (Nosan Corporation) in a sealed Tupperware container. The promoter region of the sericin 1 gene was prepared by PCR from the genomic DNA of an overproducing strain. A region approximately 1-kb upstream of the sericin 1 gene was amplified by PCR (FIG. 1) and inserted into a plasmid as the promoter region. This plasmid was amplified using $E.\ coli$ and then purified. After confirming the nucleotide sequence using an automated sequencer, the sequence was inserted upstream of the GAL4 gene. The resulting fused gene was then inserted into a plasmid vector for producing transgenic silkworms. Next, for the detection of recombinants, the 3XP3DsRed gene that is characteristically expressed in the eye was inserted into this vector (FIG. 2). Production of recombinant silkworms was performed using the method of Tamura et al. (2000). The obtained transgenic silkworms were crossed with the UAS-GFP homozygous silkworm strain produced by the method of Imamura et al. (2003), which comprises a green fluorescent protein gene as a reporter downstream of the GAL4 target sequence, UAS. Expression of GFP in recombinant silkworms was observed using a fluorescent microscope equipped with a GFP filter.

2. Results and Discussion

Figure 3:
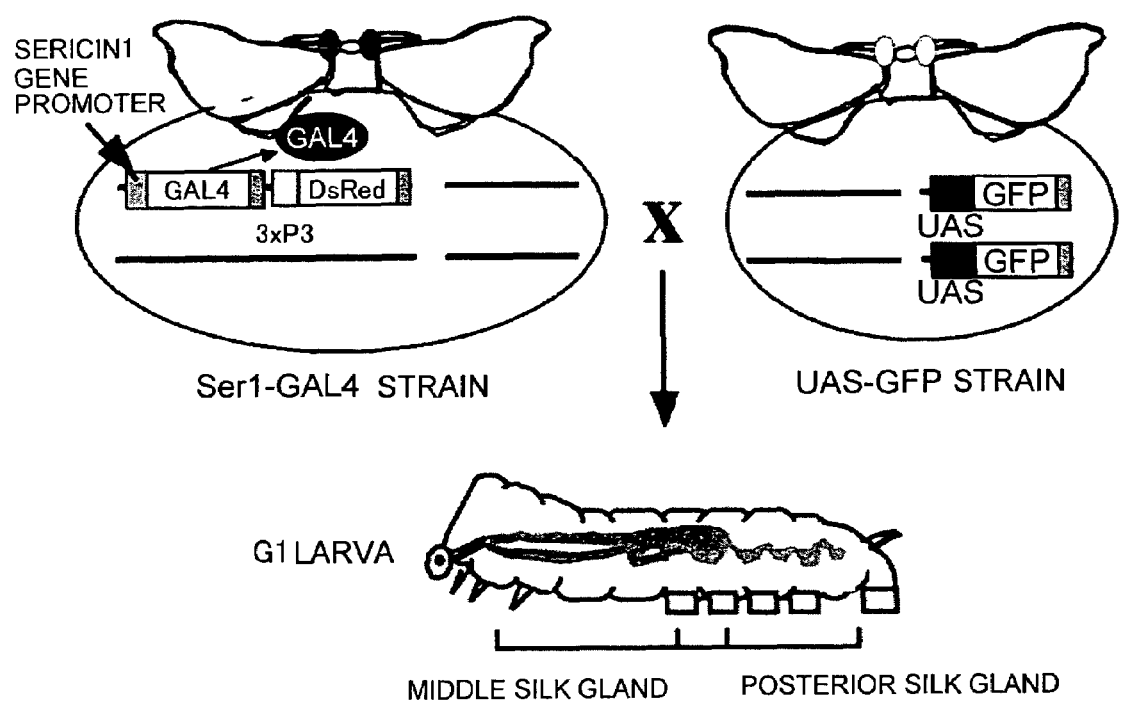
FIG. 3 shows the production of an individual carrying the GAL4 and UASGFP genes by crossing the GAL4 and UAS-GFP strains.

The structure of the produced vector is shown in FIG. 2. This plasmid vector and a helper plasmid that express a transferase for introducing genes into silkworm eggs were injected together into the eggs of the nondiapausing strain, w1-pnd, immediately after ovipositioning. Larvae that hatched from the DNA-injected eggs were reared on the artificial diet, and then the resulting moths within the experimental compartment were crossed with each other to obtain the next generation of eggs. These eggs were incubated at 25° C. Six days later, ommatidial fluorescence of embryos was observed through a fluorescence stereoscopic microscope equipped with a DsRed filter to detect individuals with eyes that emitted fluorescence. Larvae which expressed DsRed in the ommatidium immediately after hatching were selected and raised. The obtained adults were crossed with the UASGFP homozygous strain produced by Imamura et al. (2002) (FIG. 3). The GAL4 gene was inserted into a vector in combination with the marker gene, 3XP3DsRed, to produce transgenic silkworms. Therefore, the success of the incorporation of the GAL4 gene into the individuals could be determined according to whether DsRed is expressed in eyes. Furthermore, since crossing was performed with the UASGFP homozygous strain, all individuals carried the UASGFP gene.

Figure 4:
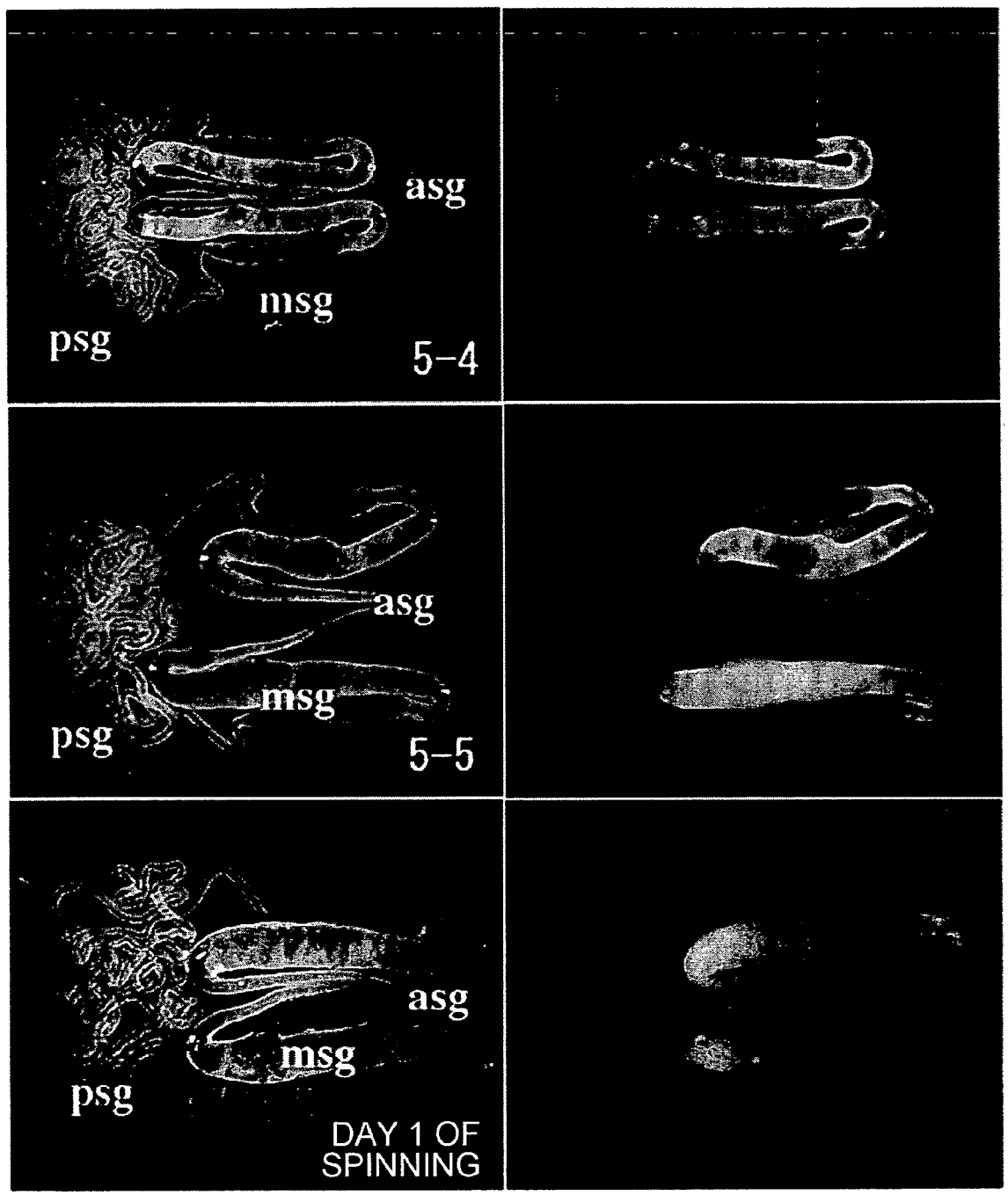
FIG. 4 is a set of photographs showing the expression of GFP in the silk gland derived from a 5th instar larva. 5-4, 5th instar day 4; 5-5, 5th instar day 5 (mature silkworm stage); and day 1 of spinning, first day of spinning.
Figure 5:
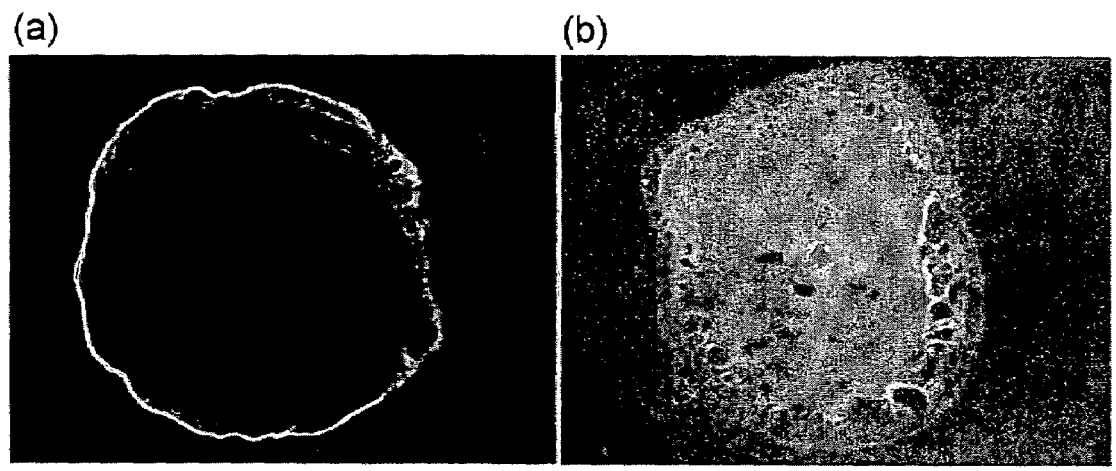
FIG. 5 is a pair of photographs showing GFP in cross sections of the middle silk gland on day 1 of spinning; (A) the central region of the middle silk gland; and (B) the anterior of the middle silk gland.
Figure 6:
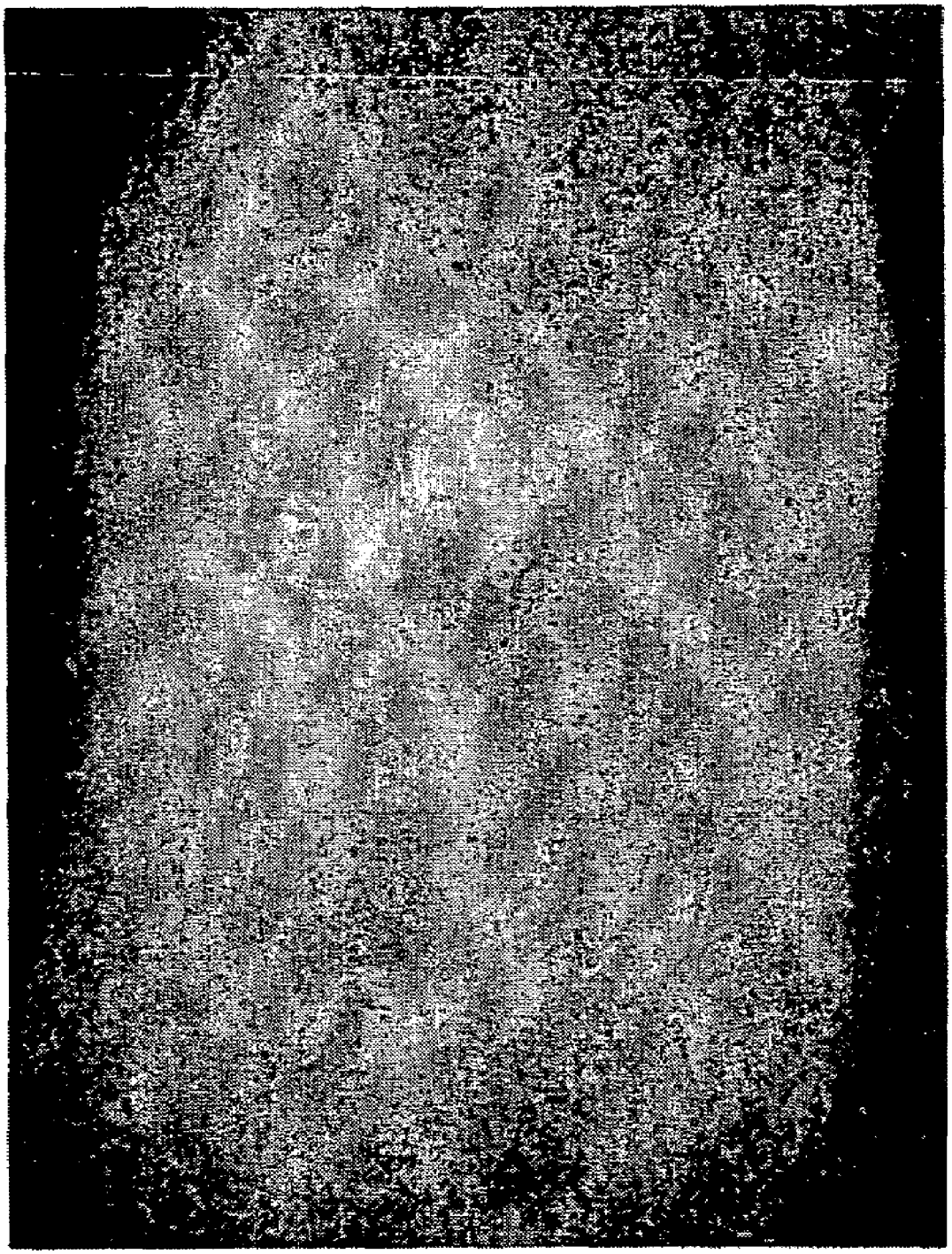
FIG. 6 is a photograph showing a cocoon made by a transgenic silkworm comprising the sericin GAL4 gene and UAS-GFP gene.

Silk glands of the last instar larvae were examined to determine whether the GFP reporter gene is expressed in the middle silk gland of the silkworm larvae of interest, and the results revealed that fluorescence was observed only in the middle silk gland of this strain (FIG. 4). The middle silk gland was examined from the 5th instar stage to the spinning stage. As indicated in FIG. 4, GFP was secreted from the middle silkgland cells starting approximately from the spinning stage, and fluorescence moved towards the anterior part of the middle silk gland. The cross-sectional view of the middle silk gland at the spinning stage also showed that GFP is secreted into the gland lumen (FIG. 5). Finally, GFP was spun as cocoon filaments and cocoons comprising a large amount of GFP were produced (FIG. 6). Despite that the GFP gene used in this study does not carry a signal sequence for secretion, large amounts of GFP were secreted into the middle silkgland lumen, and thus it is clear that GFP had been transferred to the cocoon filaments.

Example 2

Expression and Characteristics of Recombinant Proteins in the Middle Silk Gland of the Sericin Mutant Nd-s$^D$ Silkworm Strain In Example 1, a method was developed for expressing large amounts of the recombinant protein in the middle silk gland by introducing into silkworms a gene comprising the yeast GAL4 gene linked downstream of the sericin 1 gene promoter from the middle silk gland, and then crossing the silkworms with UASGFP silkworms carrying the green fluorescent protein gene as a reporter downstream of the GAL4 target sequence, UAS. In the above-described case, the protein synthesized in the middle silk gland was secreted into the lumen. In Example 2, such genes are introduced into the mutant Nd-s$^D$ strain, which secretes fibroin protein abnormally and only secretes sericin that is expressed in the middle silk gland, to produce a silkworm strain. Purification of GFP as a recombinant protein from the middle silk gland of the obtained silkworms was carried out to show that the recombinant protein can be purified easily.

1. Materials and Methods

F1 silkworms were produced by crossing an Nd-s$^D$ mutant strain with a normal strain carrying the GAL4 gene comprising the promoter of sericin gene 1 (Ser1GAL4) and a green fluorescent protein gene as a reporter downstream of target sequence UAS (UASGFP). Individuals carrying the Ser1GAL4 and UASGFP genes were identified using a fluorescence stereoscopic microscope equipped with a filter for detecting red fluorescent protein (DsRed) and green fluorescent protein (GFP), and were raised. In the next generation, obtained by crossing adults, individuals carrying the Ser1GAL4 and UASGFP genes were selected again and raised. The 5th instar silkworms were dissected to determine whether they were the mutant Nd-s$^D$ strain according to the degree of development of the posterior silk gland. The middle silk glands of the mutant Nd-s$^D$ strain individuals were removed, and under a stereoscopic microscope the whole middle silk gland was separated from its contents, and then extracted with water or 2% LDS. The extracts were stored at 5° C., and a portion of the extracts were used for detection by SDS-PAGE, and by Western blotting using a commercially available GFP antibody.

2. Results and Discussion

Figure 7:
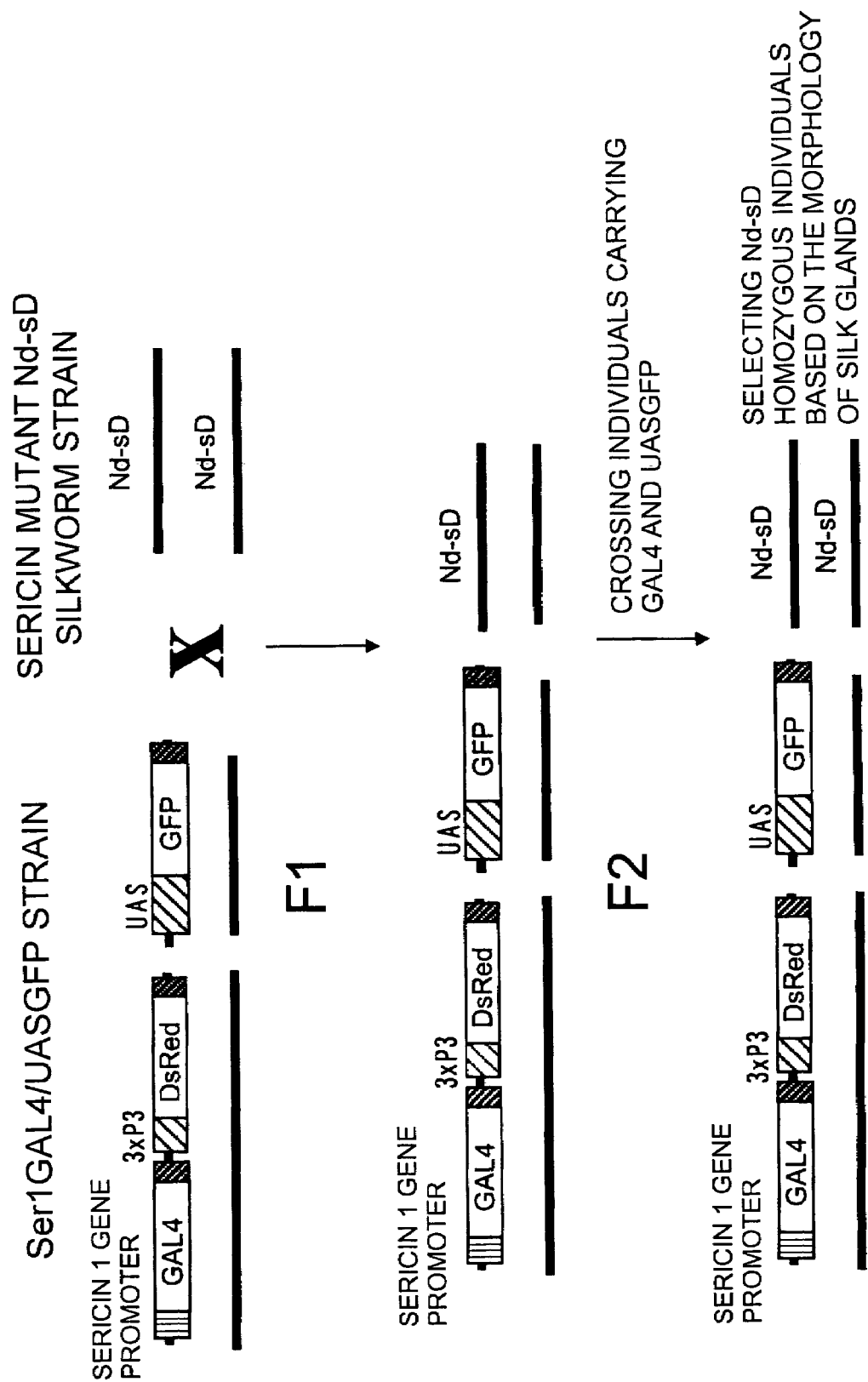
FIG. 7 shows the introduction of the Ser1GAL gene and UASGFP gene into the sericin silkworm by crossing.
Figure 8:
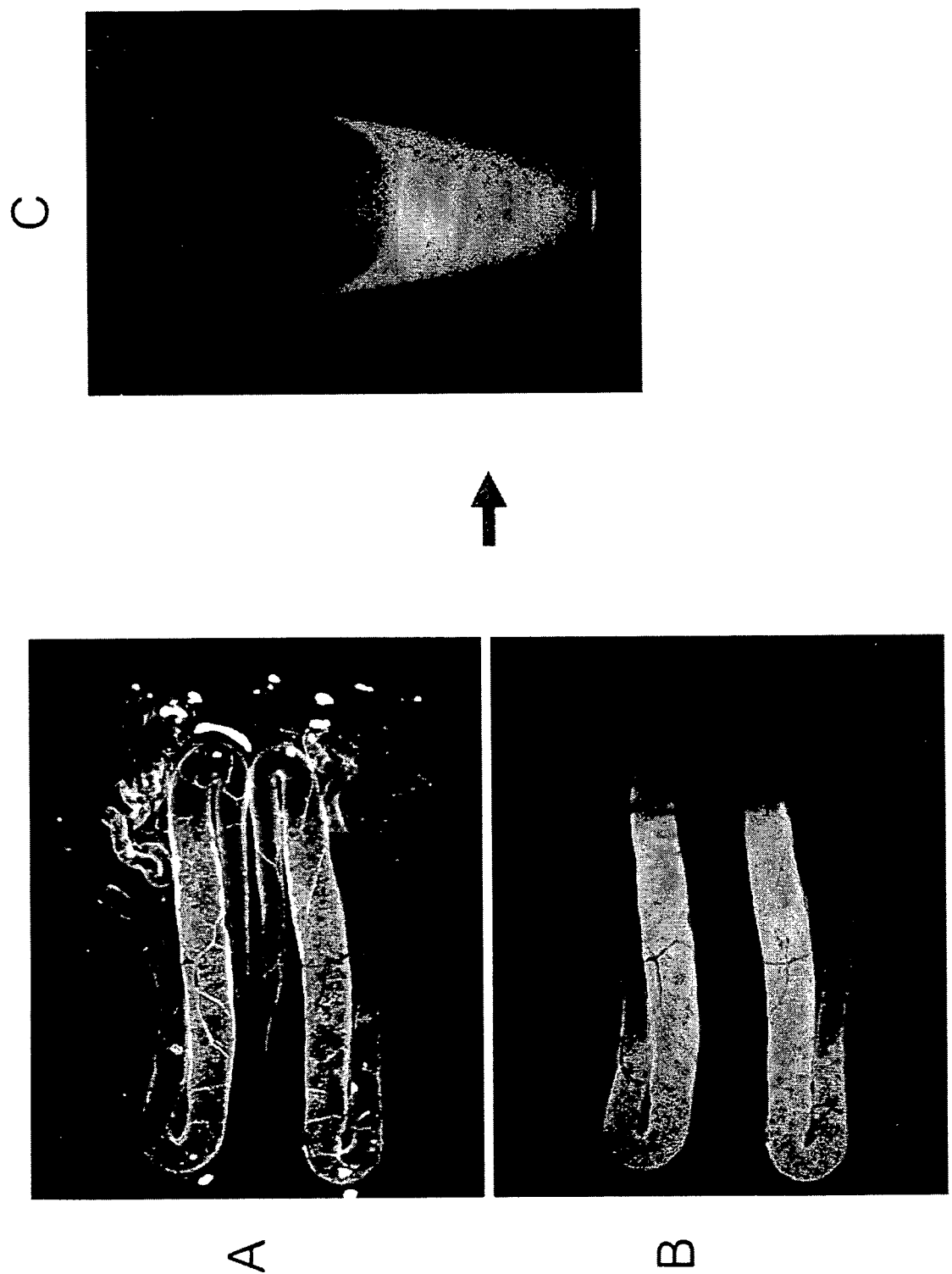
FIG. 8 is a set of photographs showing proteins extracted from the silk glands of the sericin silkworm (Nd-s$^D$). (A) a photograph of silk glands at the spinning stage under visible light (the thick portions are the middle silk glands); (B) a photograph of the silk glands of A under fluorescent light; and (C) a photograph of GFP extracted from middle silk glands, in water.
Figure 9:
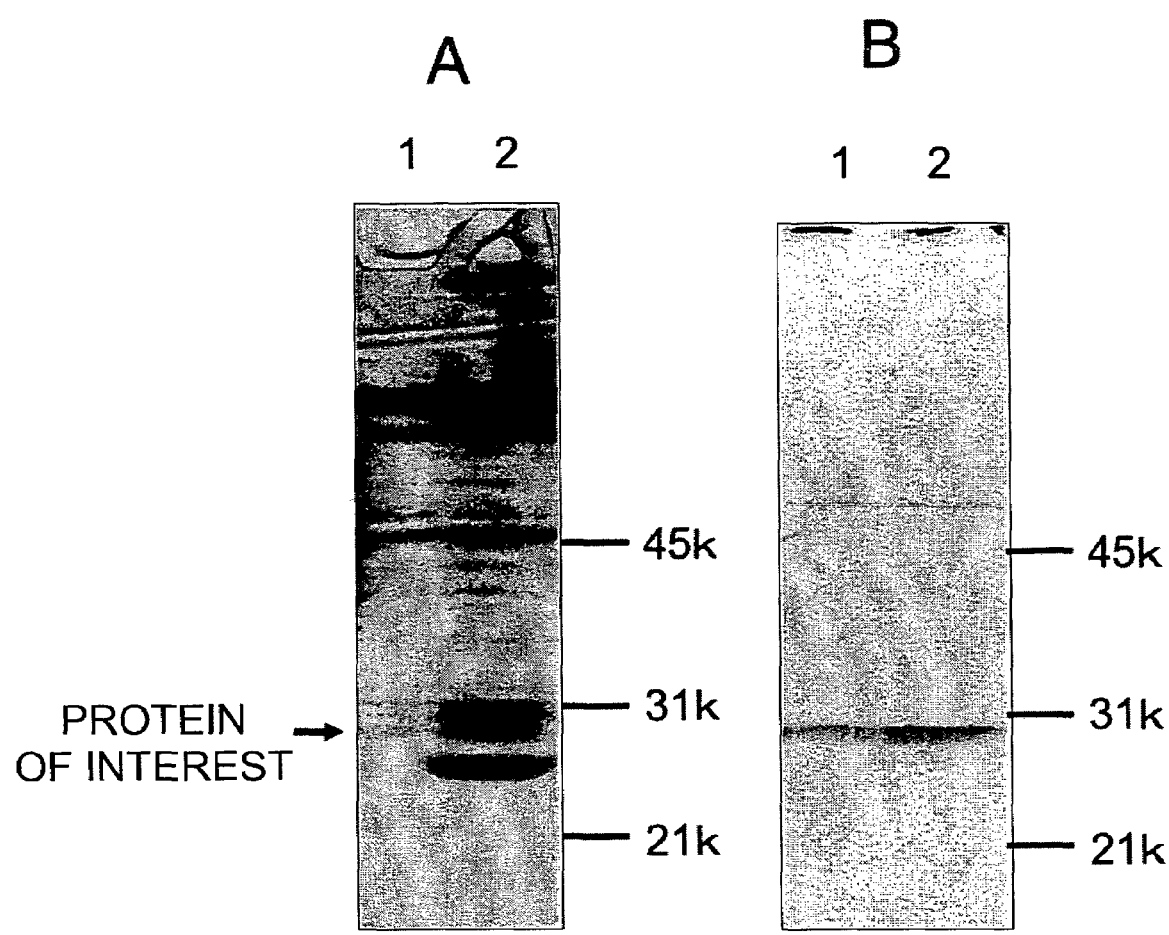
FIG. 9 is a pair of photographs showing the SDS-PAGE analysis of proteins extracted from the middle silk glands of the sericin silkworm (Nd-s$^D$) (A); and detection of the protein of interest (GFP) by Western blotting (B). Lane 1: The sample obtained by extracting the contents of the middle silk gland with water; and Lane 2: the sample obtained by extracting the content of the middle gland with 2% LDS.

FIG. 7 shows the method for producing the transgenic sericin silkworm strain comprising Ser1GAL4 and UASGFP genes following crossing. This crossing yielded the F2 individuals of interest. Fifth instar silkworms that had started to spin silk were dissected, their silk glands were examined, and the middle silk glands were found to be sufficiently developed as shown in FIG. 8A. However, the posterior silk gland was shorter than that of a normal silkworm (see, the photograph of FIG. 4 in Example 1), and had clearly degenerated. Furthermore, the middle silk gland was observed to be green under visible light, suggesting that large amounts of GFP might be produced in this tissue. By observing this silk gland using a fluorescence stereoscopic microscope, strong green fluorescence was found in the middle silk gland as expected (FIG. 8B), indicating that large amounts of GFP were present in this area. This tissue was dissected and the contents were removed using tweezers. The obtained contents were easily dissolved in water at 5° C., and more easily in 2% LDS solution. The samples dissolved in this solution were examined by SDS-PAGE. The band of interest was also observed following staining of the electrophoresed gel with Coomassie Brilliant Blue. Accordingly, large amounts of the protein of interest were found to be synthesized in the middle silk gland of the transgenic mutant Nd-s$^D$ strain (FIG. 9). Thus, by producing proteins using this mutant strain, the protein of interest is secreted into the lumen and can be extracted easily using solvents such as water, without using protein denaturants.

What is claimed is:

1. A method for producing a protein of interest, wherein the method comprises the steps of:
   (a) providing a transgenic silkworm whose genome comprises the following DNAs:
      (i) a first DNA encoding a GAL4 that is operably linked downstream of a promoter DNA comprising the nucleotide sequence of SEQ ID NO:1; and
      (ii) a second DNA encoding the protein of interest that is operably linked downstream of a UAS, wherein the transgenic silkworm secretes the protein of interest; and
   (b) recovering the secreted protein of interest produced by the transgenic silkworm.

2. A method for producing a protein of interest, wherein the method comprises the steps of:
   (a) providing a transgenic silkworm which is produced by crossing the following transgenic silkworms:
      (i) a first transgenic silkworm whose genome comprises a DNA encoding a GAL4 that is operably linked downstream of a promoter DNA comprising the nucleotide sequence of SEQ ID NO:1; and
      (ii) a second transgenic silkworm whose genome comprises a DNA encoding the protein of interest that is operably linked downstream of a UAS, wherein the transgenic silkworm secretes the protein of interest; and
   (b) recovering the secreted protein of interest produced by the transgenic silkworm.

3. A method for producing a transgenic silkworm that secretes a protein of interest into its cocoon filaments, wherein the method comprises the step of providing a silkworm egg comprising the following DNAs:
   (i) a first DNA encoding a GAL4 that is operably linked downstream of a promoter DNA comprising the nucleotide sequence of SEQ ID NO:1; and
   (ii) a second DNA encoding the protein of interest that is operably linked downstream of a UAS.

4. A method for producing a transgenic silkworm that secretes a protein of interest into its cocoon filaments, wherein the method comprises the step of providing a silkworm egg which is produced by crossing the following transgenic silkworms:
   (i) a first transgenic silkworm whose genome comprises a DNA encoding a GAL4 that is operably linked downstream of a promoter DNA comprising the nucleotide sequence of SEQ ID NO:1; and
   (ii) a second transgenic silkworm whose genome comprises a DNA encoding the protein of interest that is operably linked downstream of a UAS.

5. A transgenic silkworm whose genome comprises the following DNAs:
   (i) a first DNA encoding a GAL4 that is operably linked downstream of a promoter DNA comprising the nucleotide sequence of SEQ ID NO:1; and
   (ii) a second DNA encoding a protein of interest that is operably linked downstream of a UAS,
   wherein the transgenic silkworm expresses the protein of interest or secretes the protein of interest into its cocoon filaments.

6. A method for expressing a protein of interest in the middle silkgland cells, wherein the method comprises the steps of providing a transgenic silkworm whose genome comprises the following DNAs:
   (i) a first DNA encoding a GAL4 that is operably linked downstream of a promoter DNA comprising the nucleotide sequence of SEQ ID NO:1; and
   (ii) a second DNA encoding the protein of interest that is operably linked downstream of a UAS.

7. A method for expressing a protein of interest in the middle silkgland cells, wherein the method comprises the steps of providing a transgenic silkworm which is produced by crossing the following transgenic silkworms:
   (i) a first transgenic silkworm whose genome comprises a DNA encoding a GAL4 that is operably linked downstream of a promoter DNA comprising the nucleotide sequence of SEQ ID NO:1; and
   (ii) a second transgenic silkworm whose genome comprises a DNA encoding the protein of interest that is operably linked downstream of a UAS.

8. A method for producing a transgenic silkworm that expresses a protein of interest in the middle silkgland cells, wherein the method comprises the step of providing a silkworm egg comprising the following DNAs:
   (i) a first DNA encoding a GAL4 that is operably linked downstream of a promoter DNA comprising the nucleotide sequence of SEQ ID NO:1; and
   (ii) a second DNA encoding the protein of interest that is operably linked downstream of a UAS.

9. A method for producing a transgenic silkworm that expresses a protein of interest in the middle silkgland cells, wherein the method comprises the step of providing a silkworm egg which is produced by crossing the following transgenic silkworms:
   (i) a first transgenic silkworm whose genome comprises a DNA encoding a GAL4 that is operably linked downstream of a promoter DNA comprising the nucleotide sequence of SEQ ID NO:1; and
   (ii) a second transgenic silkworm whose genome comprises a DNA encoding the protein of interest that is operably linked downstream of a UAS.

* * * * *